US011998534B2

(12) United States Patent
Cao

(10) Patent No.: US 11,998,534 B2
(45) Date of Patent: Jun. 4, 2024

(54) GPX4 INHIBITOR IN COMBINATION WITH ANTICANCER AGENT FOR TREATING PROLIFERATIVE DISEASE

(71) Applicant: Eubulus Biotherapeutics Inc., Jiaxing (CN)

(72) Inventor: Sheldon Cao, San Diego, CA (US)

(73) Assignee: Eubulus Biotherapeutics Inc., Zhejiang (CN)

( * ) Notice: Subject to any disclaimer, the term of this patent is extended or adjusted under 35 U.S.C. 154(b) by 94 days.

(21) Appl. No.: 17/173,416

(22) Filed: Feb. 11, 2021

(65) Prior Publication Data

US 2021/0244715 A1  Aug. 12, 2021

Related U.S. Application Data

(60) Provisional application No. 62/975,732, filed on Feb. 12, 2020.

(51) Int. Cl.
*A61K 31/437* (2006.01)
*A61K 9/00* (2006.01)
*A61K 31/167* (2006.01)
*A61K 31/245* (2006.01)
*A61K 31/265* (2006.01)
*A61K 31/44* (2006.01)
*A61K 31/4709* (2006.01)
*A61P 35/00* (2006.01)

(52) U.S. Cl.
CPC .......... *A61K 31/437* (2013.01); *A61K 9/0053* (2013.01); *A61K 31/167* (2013.01); *A61K 31/245* (2013.01); *A61K 31/265* (2013.01); *A61K 31/44* (2013.01); *A61K 31/4709* (2013.01); *A61P 35/00* (2018.01)

(58) Field of Classification Search
CPC .. A61K 31/437; A61K 9/0053; A61K 31/167; A61K 31/245; A61K 31/265; A61K 1/44; A61K 1/4709; A61P 35/00
See application file for complete search history.

(56) References Cited

U.S. PATENT DOCUMENTS 10,517,872 B2 * 12/2019 Chen ................ A61P 19/06
2019/0315681 A1 * 10/2019 Stockwell ............. C07C 311/20

FOREIGN PATENT DOCUMENTS

WO  WO-2019168999 A1 * 9/2019 .......... A61K 31/437

OTHER PUBLICATIONS

Shin, D. et al. Nrf2 inhibition reverses resistance to GPX4 inhibitor-induced ferroptosis in head and neck cancer. 2018, Free Radical Biology and Medicine 129, 454-462 (Year: 2018).*
Liuji Chen, William Sealy Hambright, Ren Na, Qitao Ran, Journal of Biological Chemistry, vol. 290, Issue 47, 2015, pp. 28097-28106 (Year: 2015).*
Sui etl al. "RSL3 Drives Ferroptsos Through GPX4 Inactivation and ROS Production in Colorectal Cancer", Frontiers in Pharmacology, 2018, 9 (Year: 2018).*
Hangauer et al. "Drug-tolerant persister cancer cells are vulnerable to GPX4 inhibition." Nature, 2017, 551, 247-250 (Year: 2017).*
Smith AC, Mears AJ, Bunker R, et alMutations in the enzyme glutathione peroxidase 4 cause Sedaghatian-type spondylometaphyseal dysplasiaJournal of Medical Genetics 2014;51:470-474 (Year: 2014).*
Zou, Nature Communications, 2019, 10,:1617 (Year: 2019).*
Afinitor Package Insert (2010).
Alecensa Package Insert (2017).
Alunbrig Package Insert (2017).
Balversa Package Insert (Apr. 2020).
Berge et al., "Pharmaceutical salts," J. Pharm. Sci. 1977, 66, 1-19.
Bi et al., "Metadherin enhances vulnerability of cancer cells to ferroptosis," Cell Death Dis. 2019, 10, 682.
Bosulif Package Insert (2017).
Braftovi Package Insert (2018).
Brigelius-Flohe and Maiorino, "Glutathione peroxidases," Biochim. Biophys. Acta 2013, 1830, 3289-303.
Cabometyx Package Insert (2019).
Calquence Package Insert (2017).
Cancer Facts & Figures 2019.
Cao and Dixon, "Mechanisms of ferroptosis," Cell. Mol. Life Sci. 2016, 73, 2195-209.
Caprelsa Package Insert (2014).
Cotellic Package Insert (2015).
Dixon et al., "Ferroptosis: an iron-dependent form of nonapoptotic cell death," Cell 2012, 149, 1060-72.
Eloxatin Package Insert (Mar. 2020).
Fearnhead et al., "How do we fit ferroptosis in the family of regulated cell death?" Cell Death Differ. 2017, 24, 1991-8.
Gilotrif Package Insert (2018).
Gleevec Package Insert (2008).
Gudipaty et al., "Unconventional Ways to Live and Die: Cell Death and Survival in Development, Homeostasis, and Disease," Annu. Rev. Cell Dev. Biol. 2018, 34, 311-32.
Ibrance Package Insert (2019).
Iclusig Package Insert (Dec. 2020).
Imbruvica Package Insert (Dec. 2020).
Inlyta Package Insert (Jun. 2020).
Inrebic Package Insert (2019).
Iressa Package Insert (2019).
Jakafi Package Insert (2011).
Johnstone et al., "The next generation of platinum drugs: Targeted Pt(II) agents, nanoparticle delivery, and Pt(IV) prodrugs," Chem. Rev. 2016, 116, 3436-86.
Kisqali Package Insert (2017).
Lei et al., "Mechanisms of ferroptosis and relations with regulated cell death: A review," Front. Physiol. 2019, 10, 139.

(Continued)

*Primary Examiner* — Susanna Moore
*Assistant Examiner* — Luisalberto Gonzalez
(74) *Attorney, Agent, or Firm* — Lin Yu; Juniv LLP

(57) ABSTRACT

Provided herein is a method of treating, preventing, or ameliorating one or more symptoms of a GPX4-mediated disorder, disease, or condition in a subject with a GPX4 inhibitor and an anticancer agent. Also provided herein are methods of inducing ferroptosis in a cell or inhibiting the growth of a cell with a GPX4 inhibitor and an anticancer agent.

17 Claims, 3 Drawing Sheets

(56) References Cited

OTHER PUBLICATIONS

Lenvima Package Insert (Dec. 2020).
Lorbrena Package Insert (Mar. 2021).
Mekinist Package Insert (May 2021).
Mektovi Package Insert (2018).
Mou et al., "Ferroptosis, a new form of cell death: opportunities and challenges in cancer," J. Hematol. Oncol. 2019, 12, 34.
Nerlynx Package Insert (Feb. 2020).
Nexavar Package Insert (2018).
Ofev Package Insert (Oct. 2020).
Paraplatin Package Insert (2010).
Platinol Package Insert (2011).
Rozlytrek Package Insert (2019).
Rydapt Package Insert (2017).
Seibt et al., "Role of GPX4 in ferroptosis and its pharmacological implication," Free Radic. Biol. Med. 2019, 133, 144-52.
Skouta et al., "Ferrostatins inhibit oxidative lipid damage and cell death in diverse disease models," J. Am. Chem. Soc. 2014, 136, 4551-6.
Sprycel Package Insert (Mar. 2021).
Stivarg Package Insert (2012).
Sutent Package Insert (2011).
Tafinlar Package Insert (May 2021).
Tagrisso Package Insert (2015).
Tarceva Package Insert (2010).
Tasigna Package Insert (2010).
Torisel Package Insert (2011).
Turalio Package Insert (2019).
Tykerb Package Insert (Feb. 2021).
Verzenio Package Insert (2017).
Vitrakvi Package Insert (2018).
Vizimpro Package Insert (2018).
Votrient Package Insert (2012).
Xalkori Package Insert (Jan. 2021).
Xospata Package Insert (2018).
Yang et al., "MX1013, a dipeptide caspase inhibitor with potent in vivo antiapoptotic activity," Br. J. Pharmacol. 2003, 140, 402-12.
Yang et al., "Regulation of ferroptotic cancer cell death by GPX4," Cell 2014, 156, 317-31.
Zelboraf Package Insert (2017).
Zykadia Package Insert (2019).

* cited by examiner

GPX4 INHIBITOR IN COMBINATION WITH ANTICANCER AGENT FOR TREATING PROLIFERATIVE DISEASE

CROSS REFERENCE TO RELATED APPLICATION

This application claims the benefit of U.S. Provisional Application No. 62/975,732, filed Feb. 12, 2020; the disclosure of which is incorporated herein by reference in its entirety.

FIELD

Provided herein is a method of treating, preventing, or ameliorating one or more symptoms of a GPX4-mediated disorder, disease, or condition in a subject with a GPX4 inhibitor and an anticancer agent. Also provided herein are methods of inducing ferroptosis in a cell or inhibiting the growth of a cell with a GPX4 inhibitor and an anticancer agent.

BACKGROUND

Regulated cell death is essential for the survival of a multicellular organism. Dixon et al., *Cell* 2012, 149, 1060-72; Fearnhead et al., *Cell Death Differ.* 2017, 24, 1991-8; Gudipaty et al., *Annu. Rev. Cell Dev. Biol.* 2018, 34, 311-32; Mou et al., *J. Hematol. Oncol.* 2019, 12, 34. Ferroptosis is one type of regulated cell death characterized by loss of glutathione peroxidase 4 (GPX4) activity and accumulation of lipid peroxides. Dixon et al., *Cell* 2012, 149, 1060-72; Yang et al., *Cell* 2014, 156, 317-31. Ferroptosis dysfunction has been observed in many types of cancer, including breast cancer, colorectal cancer, diffuse large B-cell lymphoma, gastric cancer, hepatocellular carcinoma, lung cancer, and ovarian cancer. Mou et al., *J. Hematol. Oncol.* 2019, 12, 34.

GPX4, a selenoenzyme, is a negative regulator of ferroptosis. Yang et al., *Cell* 2014, 156, 317-31; Seibt et al., *Free Radic. Biol. Med.* 2019, 133, 144-52. GPX4 catalyzes the reduction of lipid peroxides and prevents ferroptosis. Brigelius-Flohe and Maiorino, *Biochim. Biophys. Acta* 2013, 1830, 3289-303; Cao and Dixon, *Cell. Mol. Life Sci.* 2016, 73, 2195-209. Small molecule GPX4 inhibitors (e.g., RSL3 and ML162) have been shown to be able to induce ferroptosis and suppress tumor growth in xenograft models. Yang et al., *Cell* 2014, 156, 317-31; Lei et al., *Front. Physiol.* 2019, 10, 139; Bi et al., *Cell Death Disease* 2019, 10, 682.

Despite the advances in cancer treatment, cancer remains a major worldwide public health problem. It was estimated that there will be 1,762,450 new cancer cases diagnosed and 606,880 cancer deaths in the US alone in 2019. *Cancer Facts & Figures* 2019. Therefore, there is a need for an effective therapy for cancer treatment.

SUMMARY OF THE DISCLOSURE

Provided herein is a method of treating, preventing, or ameliorating one or more symptoms of a disorder, disease, or condition mediated by a glutathione peroxidase 4 (GPX4) in a subject, comprising administering to the subject a therapeutically effective amount of a GPX4 inhibitor and a therapeutically effective amount of an anticancer agent.

Also provided herein is a method of treating, preventing, or ameliorating one or more symptoms of a proliferative disease in a subject, comprising administering to the subject a therapeutically effective amount of a GPX4 inhibitor and a therapeutically effective amount of an anticancer agent.

Additionally, provided herein is a method of inhibiting the growth of a cell, comprising contacting the cell with an effective amount of a GPX4 inhibitor and an effective amount of an anticancer agent.

Furthermore, provided herein is a method of inducing ferroptosis in a cell, comprising contacting the cell with an effective amount of a GPX4 inhibitor and an effective amount of an anticancer agent.

Provided herein is a method of treating, preventing, or ameliorating one or more symptoms of a disorder, disease, or condition mediated by a GPX4 in a subject, comprising administering to the subject a therapeutically effective amount of a GPX4 inhibitor and a subtherapeutically effective amount of an anticancer agent.

Provided herein is a method of treating, preventing, or ameliorating one or more symptoms of a proliferative disease in a subject, comprising administering to the subject a therapeutically effective amount of a GPX4 inhibitor and a subtherapeutically effective amount of an anticancer agent.

Provided herein is a method of inhibiting the growth of a cell, comprising contacting the cell with an effective amount of a GPX4 inhibitor and a subeffective amount of an anticancer agent.

Furthermore, provided herein is a method of inducing ferroptosis in a cell, comprising contacting the cell with an effective amount of a GPX4 inhibitor and a subeffective amount of an anticancer agent.

DETAILED DESCRIPTION

Figure 1:
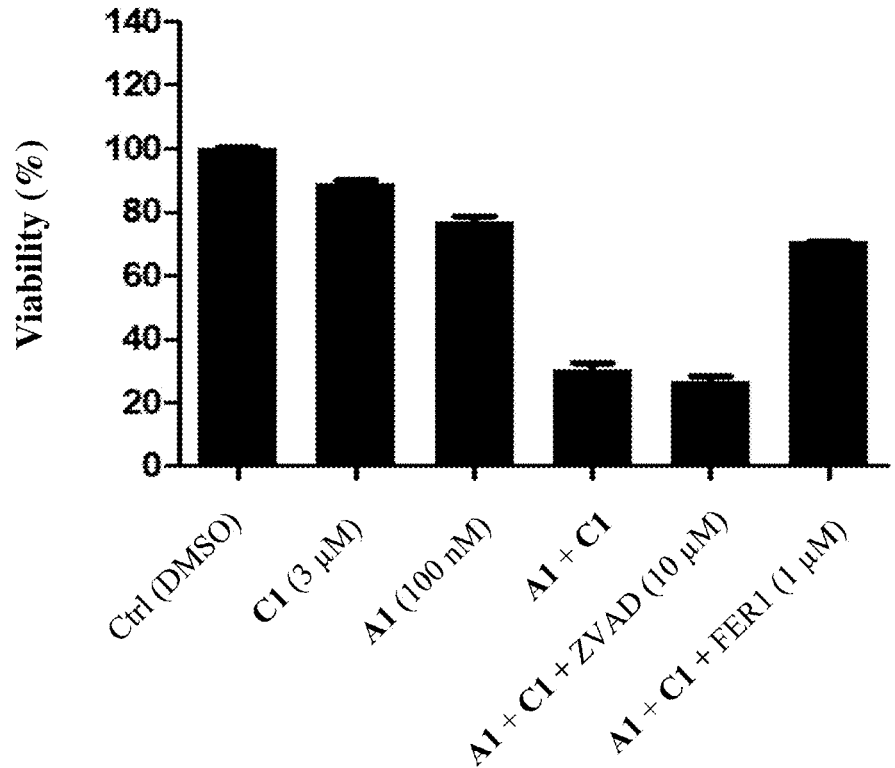
FIG. 1 shows the effects of GPX4 inhibitor A1 (100 nM) alone and in combination with sorafenib C1 (3 µM) on the viability of Huh-7 cells, where FER1 represents ferrostatin-1, a ferroptosis inhibitor (see Skouta et al., *J. Am. Chem. Soc.* 2014, 136, 4551-4556); and ZVAD represents Z-VAD-FMK, an apoptosis inhibitor (see Yang et al., *Br. J. Pharmacol.* 2003, 140, 402-412).

To facilitate understanding of the disclosure set forth herein, a number of terms are defined below.

Generally, the nomenclature used herein and the laboratory procedures in medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The terms "subeffective amount" and "subtherapeutically effective amount" of a compound are used interchangeably herein and refer to a dose of a compound that is lower than the amount that is effective when the compound is administered alone (e.g., monotherapy).

The term "$IC_{50}$" or "$EC_{50}$" refers to an amount, concentration, or dosage of a compound that is required for 50% inhibition of a maximal response in an assay that measures such a response.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, and commensurate with a reasonable benefit/risk ratio. See, e.g., *Remington: The Science and Practice of Pharmacy,* 22nd ed.; Allen Ed.; Pharmaceutical Press: London, 2012; *Handbook of Pharmaceutical Excipients,* 8th ed.; Sheskey et al., Eds.; Pharmaceutical Press: London, 2017; *Handbook of Pharmaceutical Additives,* 3rd ed.; Ash and Ash Eds.; Synapse Information Resources: 2007; *Pharmaceutical Preformulation and Formulation,* 2nd ed.; Gibson Ed.; Drugs and the Pharmaceutical Sciences 199; Informa Healthcare: New York, N.Y., 2009.

The term "about" or "approximately" means an acceptable error for a particular value as determined by one of ordinary skill in the art, which depends in part on how the value is measured or determined. In certain embodiments, the term "about" or "approximately" means within 1, 2, or 3 standard deviations. In certain embodiments, the term "about" or "approximately" means within 25%, 20%, 15%, 10%, 9%, 8%, 7%, 6%, 5%, 4%, 3%, 2%, 1%, 0.5%, or 0.05% of a given value or range.

In certain embodiments, "optically active" and "enantiomerically active" refer to a collection of molecules, which has an enantiomeric excess of no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question. In certain embodiments, an optically active compound comprises about 98% or more of one enantiomer and about 2% or less of the other enantiomer based on the total weight of the enantiomeric mixture in question. In certain embodiments, an optically active compound comprises about 99% or more of one enantiomer and about 1% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^1H$), deuterium ($^2H$), tritium ($^3H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123

($^{123}$I), iodine-125 ($^{125}$I), iodine-127 ($^{127}$I), iodine-129 ($^{129}$I), and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen ($^{1}$H), deuterium ($^{2}$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an isotopically enriched compound is in an unstable form, that is, radioactive. In certain embodiments, an isotopically enriched compound contains unnatural proportions of one or more isotopes, including, but not limited to, tritium ($^{3}$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^{2}$H, as example, or any carbon can be $^{13}$C, as example, or any nitrogen can be $^{15}$N, as example, or any oxygen can be $^{18}$O, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^{1}$H for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium ($^{1}$H), deuterium ($^{2}$H or D), and tritium ($^{3}$H), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}$C) and carbon-13 ($^{13}$C) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}$C enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%). The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 95%, at least about 96%, at least about 97%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which are present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof" has the same meaning as the phrase "(i) an enantiomer, a mixture of enantiomers, a diastereomer, a mixture of two or more diastereomers, a tautomer, a mixture of two or more tautomers, or an isotopic variant of the compound referenced therein; or (ii) a pharmaceutically acceptable salt, solvate, hydrate, or prodrug of the compound referenced therein, or (iii) a pharmaceutically acceptable salt, solvate, hydrate, or prodrug of an enantiomer, a mixture of enantiomers, a diastereomer, a mixture of two or more diastereomers, a tautomer, a mixture of two or more tautomers, or an isotopic variant of the compound referenced therein."

GPX4 Inhibitors

In one embodiment, a GPX4 inhibitor is described herein that is methyl (3R)-2-(2-chloroacetyl)-2,3,4,9-tetrahydro-1-(4-(methoxycarbonyl)phenyl)-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

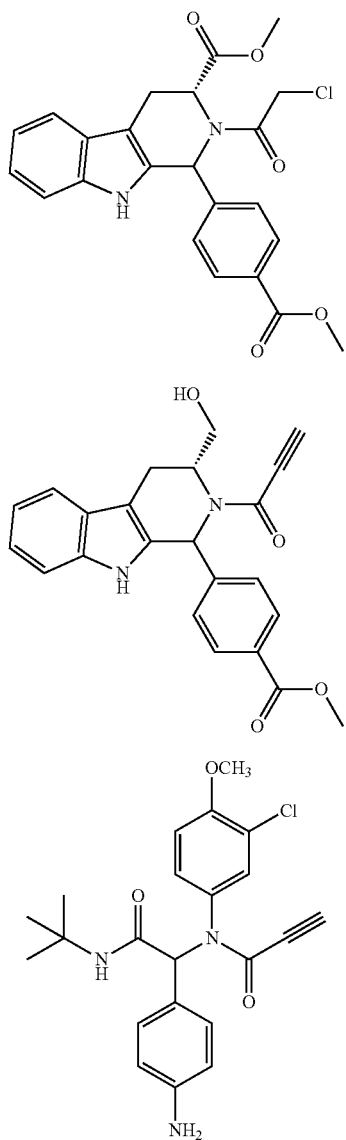

A1

A2

A3

In one embodiment, the GPX4 inhibitor described herein is methyl (3R)-2-(2-chloroacetyl)-2,3,4,9-tetrahydro-1-(4-(methoxycarbonyl)phenyl)-1H-pyrido[3,4-b]indole-3-car- boxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof.

In another embodiment, the GPX4 inhibitor described herein is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, the GPX4 inhibitor described herein is N-(1-(4-aminophenyl)-2-(tert-butylamino)-2-oxoethyl)-N-(3-chloro-4-methoxyphenyl)propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the GPX4 inhibitor described herein is deuterium enriched. In certain embodiments, the GPX4 inhibitor described herein is carbon-13 enriched. In certain embodiments, the GPX4 inhibitor described herein is carbon-14 enriched. In certain embodiments, the GPX4 inhibitor described herein contains one or more less prevalent isotopes for other elements, including, but not limited to, $^{15}N$ for nitrogen; $^{17}O$ or $^{18}O$ for oxygen, and $^{34}S$, $^{35}S$, or $^{36}S$ for sulfur.

In certain embodiments, the GPX4 inhibitor described herein has an isotopic enrichment factor of no less than about 5, no less than about 10, no less than about 20, no less than about 50, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when the GPX4 inhibitor at a given position is 100% enriched with the specified isotope. Thus, the maximum isotopic enrichment factor is different for different isotopes. The maximum isotopic enrichment factor is 6,410 for deuterium and 90 for carbon-13.

In certain embodiments, the GPX4 inhibitor described herein has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy. In certain embodiments, at least one of the atoms of the GPX4 inhibitor described herein, as specified as deuterium-enriched, has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, the GPX4 inhibitor described herein is isolated or purified. In certain embodiments, the GPX4 inhibitor described herein has a purity of at least about 90%, at least about 95%, at least about 98%, at least about 99%, or at least about 99.5% by weight.

The GPX4 inhibitor described herein is intended to encompass all possible stereoisomers unless a particular stereochemistry is specified. Where the GPX4 inhibitor described herein contains an alkenyl group, it may exist as one or mixture of geometric cis/trans (or Z/E) isomers. Where structural isomers are interconvertible, the GPX4 inhibitor may exist as a single tautomer or a mixture of tautomers. This can take the form of proton tautomerism in the GPX4 inhibitor that contains, for example, an imino, keto, or oxime group; or so-called valence tautomerism in the GPX4 inhibitor that contains an aromatic moiety. It follows that a single GPX4 inhibitor may exhibit more than one type of isomerism.

The GPX4 inhibitor described herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for the GPX4 inhibitor that undergoes epimerization in vivo, to administration of the GPX4 inhibitor in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the GPX4 inhibitor described herein contains an acidic or basic moiety, it can also be provided as a pharmaceutically acceptable salt. See, Berge et al., *J. Pharm. Sci.* 1977, 66, 1-19; *Handbook of Pharmaceutical Salts: Properties, Selection, and Use*, 2nd ed.; Stahl and Wermuth Eds.; John Wiley & Sons, 2011. In certain embodiments, a pharmaceutically acceptable salt of the GPX4 inhibitor described herein is a solvate. In certain embodiments, a pharmaceutically acceptable salt of the GPX4 inhibitor described herein is a hydrate.

Suitable acids for use in the preparation of pharmaceutically acceptable salts of a GPX4 inhibitor described herein include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts of a GPX4 inhibitor described herein include, but are not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

A GPX4 inhibitor described herein may also be provided as a prodrug, which is a functional derivative of the GPX4 inhibitor and is readily convertible into the parent GPX4 inhibitor in vivo. Prodrugs are often useful because, in some situations, they may be easier to administer than the parent GPX4 inhibitor. They may, for instance, be bioavailable by oral administration whereas the parent GPX4 inhibitor is not. The prodrug may also have enhanced solubility in pharmaceutical compositions over the parent GPX4 inhibitor. A prodrug may be converted into the parent drug by various mechanisms, including enzymatic processes and metabolic hydrolysis.

In one embodiment, a GPX4 inhibitor described herein is provided as a pharmaceutical composition comprising the GPX4 inhibitor, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

In one embodiment, the pharmaceutical composition provided herein comprises methyl (3R)-2-(2-chloroacetyl)-2,3,4,9-tetrahydro-1-(4-(methoxycarbonyl)phenyl)-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

In another embodiment, the pharmaceutical composition provided herein comprises methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

In yet another embodiment, the pharmaceutical composition provided herein comprises N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

The GPX4 inhibitor-pharmaceutical composition provided herein can be formulated in various dosage forms, including, but not limited to, dosage forms for oral, parenteral, and topical administration. The GPX4 inhibitor-pharmaceutical composition provided herein can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art. See, e.g., *Remington: The Science and Practice of Pharmacy*, supra; *Modified-Release Drug Delivery Technology*, 2nd Edition, Rathbone et al., Eds., Marcel Dekker, Inc.: New York, N.Y., 2008.

In one embodiment, the GPX4 inhibitor-pharmaceutical composition provided herein is formulated in a dosage form for oral administration. In another embodiment, GPX4 inhibitor-pharmaceutical composition provided herein is formulated as a tablet, capsule, or solution for oral administration. In yet another embodiment, the GPX4 inhibitor-pharmaceutical composition provided herein is formulated as a tablet. In yet another embodiment, the GPX4 inhibitor-pharmaceutical composition provided herein is formulated as a capsule. In yet another embodiment, the GPX4 inhibitor-pharmaceutical composition provided herein is formulated as a solution. In yet another embodiment, the GPX4 inhibitor-pharmaceutical composition provided herein is formulated in a dosage form for parenteral administration. In yet another embodiment, the GPX4 inhibitor-pharmaceutical composition provided herein is formulated in a dosage form for intravenous administration. In yet another embodiment, the GPX4 inhibitor-pharmaceutical composition provided herein is formulated in a dosage form for intramuscular administration. In yet another embodiment, the GPX4 inhibitor-pharmaceutical composition provided herein is formulated in a dosage form for subcutaneous administration. In still another embodiment, the GPX4 inhibitor-pharmaceutical composition provided herein is formulated in a dosage form for topical administration.

The GPX4 inhibitor-pharmaceutical composition provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The GPX4 inhibitor-pharmaceutical composition provided herein can be administered at once, or multiple times at intervals of time. It is understood that the precise dosage and duration of treatment may vary with the age, weight, and condition of the subject being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the GPX4 inhibitor-pharmaceutical composition.

Anticancer Agents

In one embodiment, an anticancer agent described herein is a kinase inhibitor. In another embodiment, the anticancer agent described herein is a protein kinase inhibitor. In yet another embodiment, the anticancer agent described herein is a tyrosine kinase inhibitor. In still another embodiment, the anticancer agent described herein is a serine/threonine kinase inhibitor.

In one embodiment, the anticancer agent is a multi-kinase inhibitor. In another embodiment, the anticancer agent is a multi-protein kinase inhibitor. In yet another embodiment, the anticancer agent is a multi-tyrosine kinase inhibitor. In still another embodiment, the anticancer agent is a multi-serine/threonine kinase inhibitor.

In certain embodiments, the anticancer agent is an ALK inhibitor, an AXL inhibitor, a BCR-ABL inhibitor, a BRAF inhibitor, a BTK inhibitor, a CDK inhibitor, an EGFR inhibitor, a FGFR inhibitor, a HER inhibitor, a JAK inhibitor, a MEK inhibitor, a MET inhibitor, an mTOR inhibitor, a TRK inhibitor, a PDGFR inhibitor, a RET inhibitor, a SRC inhibitor, or a VEGFR inhibitor.

In certain embodiments, the anticancer agent is an ALK inhibitor, e.g., alectinib, brigatinib, ceritinib, crizotinib, entrectinib, or lorlatinib. In certain embodiments, the anticancer agent is an AXL inhibitor, e.g., gilteritinib. In certain embodiments, the anticancer agent is a BCR-ABL inhibitor, e.g., bosutinib, dasatinib, imatinib, nilotinib, or ponatinib. In certain embodiments, the anticancer agent is a BRAF inhibitor, e.g., dabrafenib, encorafenib, or vemurafenib. In certain embodiments, the anticancer agent is a BTK inhibitor, e.g., acalabrutinib or ibrutinib. In certain embodiments, the anticancer agent is a CDK inhibitor, e.g., abemaciclib, palbociclib, ribociclib, or sorafenib. In certain embodiments, the anticancer agent is a MET inhibitor, e.g., cabozantinib or crizotinib. In certain embodiments, the anticancer agent is an EGFR inhibitor, e.g., afatinib, dacomitinib, erlotinib, gefitinib, lapatinib, osimertinib, or vandetanib. In certain embodiments, the anticancer agent is a FGFR inhibitor, e.g., erdafitinib. In certain embodiments, the anticancer agent is a HER inhibitor, e.g., dacomitinib, lapatinib, or neratinib. In certain embodiments, the anticancer agent is a JAK inhibitor, e.g., fedratinib or ruxolitinib. In certain embodiments, the anticancer agent is a MEK inhibitor, e.g., binimetinib, cobimetinib, or trametinib. In certain embodiments, the anticancer agent is an mTOR inhibitor, e.g., everolimus or temsirolimus. In certain embodiments, the anticancer agent is a PDGFR inhibitor, e.g., axitinib, gefitinib, imatinib, lenvatinib, nintedanib, pazopanib, regorafenib, sorafenib, or sunitinib. In certain embodiments, the anticancer agent is a RET inhibitor, e.g., vandetanib. In certain embodiments, the anticancer agent is a SRC inhibitor, e.g., bosutinib, dasatinib, ponatinib, or vandetanib. In certain embodiments, the anticancer agent is a TRK inhibitor, e.g., larotrectinib. In certain embodiments, the anticancer agent is a VEGFR inhibitor, e.g., axitinib, lenvatinib, nintedanib, pazopanib, regorafenib, sorafenib, or sunitinib.

In certain embodiments, the anticancer agent is abemaciclib, acalabrutinib, afatinib, alectinib, axitinib, binimetinib, brigatinib, bosutinib, cabozantinib, ceritinib, cobimetinib, crizotinib, dabrafenib, dacomitinib, dasatinib, encorafenib, entrectinib, erdafitinib, erlotinib, everolimus, fedratinib, gefitinib, gilteritinib, ibrutinib, imatinib, lapatinib, larotrectinib, lenvatinib, lorlatinib, midostaurin, neratinib, nilotinib, nintedanib, osimertinib, palbociclib, pazopanib, pexidartinib, ponatinib, regorafenib, ribociclib, ruxolitinib, sorafenib, sunitinib, temsirolimus, trametinib, vandetanib, or vemurafenib.

In certain embodiments, the anticancer agent is axitinib, gefitinib, imatinib, lenvatinib, neratinib, nintedanib, palbociclib, pazopanib, regorafenib, ribociclib, sorafenib, or sunitinib. In certain embodiments, the anticancer agent is axitinib, gefitinib, imatinib, lenvatinib, neratinib, nintedanib, pazopanib, regorafenib, sorafenib, or sunitinib. In certain embodiments, the anticancer agent is neratinib, regorafenib, or sorafenib.

In one embodiment, the anticancer agent described herein is a platinum compound. In certain embodiments, the platinum compound described herein is carboplatin, cisplatin, ethacraplatin, heptaplatin, iproplatin, lobaplatin, mitaplatin, nedaplatin, ormaplatin, oxaliplatin, phenanthriplatin, picoplatin, pyriplatin, satrplatin, or triplatin tetranitrate. In certain embodiments, the platinum compound described herein is carboplatin, cisplatin, heptaplatin, lobaplatin, nedaplatin, or oxaliplatin. In certain embodiments, the platinum compound described herein is carboplatin, cisplatin, nedaplatin, or oxaliplatin. Additional platinum compounds that are suitable for use in a method provided herein are disclosed in Johnstone et al., *Chem. Rev.* 2016, 116, 3436-3486, the disclosure of which is incorporated herein by reference in its entirety.

In certain embodiments, the anticancer agent is deuterium enriched. In certain embodiments, the anticancer agent is carbon-13 enriched. In certain embodiments, the anticancer agent is carbon-14 enriched. In certain embodiments, the anticancer agent contains one or more less prevalent isotopes for other elements, including, but not limited to, $^{15}N$ for nitrogen; $^{17}O$ or $^{18}O$ for oxygen, and $^{33}S$, $^{34}S$, or $^{36}S$ for sulfur.

In certain embodiments, the anticancer agent has an isotopic enrichment factor of no less than about 5, no less than about 10, no less than about 20, no less than about 30, no less than about 40, no less than about 50, no less than about 60, no less than about 70, no less than about 80, no less than about 90, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when the anticancer agent at a given position is 100% enriched with the specified isotope. Thus, the maximum isotopic enrichment factor is different for different isotopes. The maximum isotopic enrichment factor is 6410 for deuterium and 90 for carbon-13.

In certain embodiments, the anticancer agent has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy.

In certain embodiments, the anticancer agent has a carbon-13 enrichment factor of no less than about 1.8 (about 2% carbon-13 enrichment), no less than about 4.5 (about 5% carbon-13 enrichment), no less than about 9 (about 10% carbon-13 enrichment), no less than about 18 (about 20% carbon-13 enrichment), no less than about 45 (about 50% carbon-13 enrichment), no less than about 68 (about 75% carbon-13 enrichment), no less than about 72 (about 80% carbon-13 enrichment), no less than about 77 (about 85% carbon-13 enrichment), no less than about 81 (about 90% carbon-13 enrichment), no less than about 86 (about 95% carbon-13 enrichment), no less than about 87 (about 97% carbon-13 enrichment), no less than about 88 (about 98% carbon-13 enrichment), no less than about 89 (about 99% carbon-13 enrichment), or no less than about 90 (about 99.5% carbon-13 enrichment). The carbon-13 enrichment can be determined using conventional analytical methods known to one of ordinary skill in the art, including mass spectrometry and nuclear magnetic resonance spectroscopy.

In certain embodiments, at least one of the atoms of the anticancer agent as specified as isotopically enriched has isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of the anticancer agent as specified as isotopically enriched have isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In any events, the isotopic enrichment of the isotopically enriched atom of the anticancer agent is no less than the natural abundance of the isotope specified.

In certain embodiments, at least one of the atoms of the anticancer agent as specified as deuterium-enriched has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of the anticancer agent as specified as deuterium-enriched have deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, at least one of the atoms of the anticancer agent as specified as $^{13}C$-enriched has carbon-13 enrichment of no less than about 2%, no less than about 5%, no less than about 10%, no less than about 20%, no less than about 50%, no less than about 70%, no less than about 80%, no less than about 90%, or no less than about 98%. In certain embodiments, the atoms of the anticancer agent as specified as $^{13}C$-enriched have carbon-13 enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, the anticancer agent is isolated or purified. In certain embodiments, the anticancer agent has a purity of at least about 50%, at least about 70%, at least about 80%, at least about 90%, at least about 95%, at least about 98%, at least about 99%, or at least about 99.5% by weight.

The anticancer agents described herein are intended to encompass all possible stereoisomers unless a particular stereochemistry is specified. Where the anticancer agent contains an alkenyl group, the anticancer agent may exist as one or mixture of geometric cis/trans (or Z/E) isomers. Where structural isomers are interconvertible, the anticancer agent may exist as a single tautomer or a mixture of tautomers. This can take the form of proton tautomerism in the anticancer agent that contains, for example, an imino, keto, or oxime group; or so-called valence tautomerism in the anticancer agent that contain an aromatic moiety. It follows that a single anticancer agent may exhibit more than one type of isomerism.

The anticancer agent can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of an anticancer agent in its (R) form is equivalent, for anticancer agents that undergo epimerization in vivo, to administration of the anticancer agent in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the anticancer agent contains an acidic or basic moiety, it can also be provided as a pharmaceutically acceptable salt. See, Berge et al., *J. Pharm. Sci.* 1977, 66, 1-19; *Handbook of Pharmaceutical Salts: Properties, Selection, and Use,* 2nd ed.; Stahl and Wermuth Eds.; Wiley-VCH and VHCA, Zurich, 2011.

Suitable acids for use in the preparation of pharmaceutically acceptable salts of the anticancer agent include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts of the anticancer agent, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

The anticancer agent may also be provided as a prodrug, which is a functional derivative of an anticancer agent and is readily convertible into the parent anticancer agent in vivo. Prodrugs are often useful because, in some situations, they may be easier to administer than the parent anticancer agent. They may, for instance, be bioavailable by oral administration whereas the parent anticancer agent is not. The prodrug may also have enhanced solubility in pharmaceutical compositions over the parent anticancer agent. A prodrug may be converted into the parent drug by various mechanisms, including enzymatic processes and metabolic hydrolysis.

In certain embodiments, abemaciclib or a pharmaceutically acceptable salt is formulated as described in the package insert for VERZENIO®. In certain embodiments, acalabrutinib or a pharmaceutically acceptable salt is formulated as described in the package insert for CALQUENCE®. In certain embodiments, afatinib or a pharmaceutically acceptable salt is formulated as described in the package insert for GILOTRIF®. In certain embodiments, alectinib or a pharmaceutically acceptable salt is formulated as described in the package insert for ALECENSA®. In certain embodiments, axitinib or a pharmaceutically acceptable salt is formulated as described in the package insert for INLYTA®. In certain embodiments, binimetinib or a pharmaceutically acceptable salt is formulated as described in the package insert for MEKTOVI®. In certain embodiments, brigatinib or a pharmaceutically acceptable salt is formulated as described in the package insert for ALUNBRIG®.

In certain embodiments, bosutinib or a pharmaceutically acceptable salt is formulated as described in the package insert for SOFULIF®. In certain embodiments, cabozantinib or a pharmaceutically acceptable salt is formulated as described in the package insert for CABOMETYX®. In certain embodiments, ceritinib or a pharmaceutically acceptable salt is formulated as described in the package insert for ZYKADIA®. In certain embodiments, cobimetinib or a pharmaceutically acceptable salt is formulated as described in the package insert for COTELLIC®. In certain embodiments, crizotinib or a pharmaceutically acceptable salt is formulated as described in the package insert for XALKORI®. In certain embodiments, dabrafenib or a pharmaceutically acceptable salt is formulated as described in the package insert for TAFINLAR®. In certain embodiments, dacomitinib or a pharmaceutically acceptable salt is formulated as described in the package insert for VIZIMPRO®. In certain embodiments, dasatinib or a pharmaceutically acceptable salt is formulated as described in the package insert for SPRYCEL®. In certain embodiments, encorafenib or a pharmaceutically acceptable salt is formulated as described in the package insert for BRAFTOVI®.

In certain embodiments, entrectinib or a pharmaceutically acceptable salt is formulated as described in the package insert for RAZLYTREK®. In certain embodiments, erdafitinib or a pharmaceutically acceptable salt is formulated as described in the package insert for BALVERSA®. In certain embodiments, erlotinib or a pharmaceutically acceptable salt is formulated as described in the package insert for TARCEVA®. In certain embodiments, everolimus or a pharmaceutically acceptable salt is formulated as described in the package insert for AFINITOR®. In certain embodiments, fedratinib or a pharmaceutically acceptable salt is formulated as described in the package insert for INREBIC®. In certain embodiments, gefitinib or a pharmaceutically acceptable salt is formulated as described in the package insert for IRESSA®. In certain embodiments, gilteritinib or a pharmaceutically acceptable salt is formulated as described in the package insert for XOSPATA®. In certain embodiments, ibrutinib or a pharmaceutically acceptable salt is formulated as described in the package insert for IMBRUVICA®. In certain embodiments, imatinib or a pharmaceutically acceptable salt is formulated as described in the package insert for GLEEVEC®. In certain embodiments, lapatinib or a pharmaceutically acceptable salt is formulated as described in the package insert for TYKERB®. In certain embodiments, larotrectinib or a pharmaceutically acceptable salt is formulated as described in the package insert for VITRAKVI®. In certain embodiments, lenvatinib or a pharmaceutically acceptable salt is formulated as described in the package insert for LENVIMA®. In certain embodiments, lorlatinib or a pharmaceutically acceptable salt is formulated as described in the package insert for LORBRENA®. In certain embodiments, midostaurin or a pharmaceutically acceptable salt is formulated as described in the package insert for RYDAPT®. In certain embodiments, neratinib or a pharmaceutically acceptable salt is formulated as described in the package insert for NERLYNX®. In certain embodiments, nilotinib or a pharmaceutically acceptable salt is formulated as described in the package insert for TASIGNA®. In certain embodiments, nintedanib or a pharmaceutically acceptable salt is formulated as described in the package insert for OFEV®.

In certain embodiments, osimertinib or a pharmaceutically acceptable salt is formulated as described in the package insert for TAGRISSO®. In certain embodiments, palbociclib or a pharmaceutically acceptable salt is formulated as described in the package insert for IBRANCE®. In certain embodiments, pazopanib or a pharmaceutically acceptable salt is formulated as described in the package insert for VOTRIENT®. In certain embodiments, pexidartinib or a pharmaceutically acceptable salt is formulated as described in the package insert for TURALIO®. In certain embodiments, ponatinib or a pharmaceutically acceptable salt is formulated as described in the package insert for ICLUSIG®. In certain embodiments, regorafenib or a pharmaceutically acceptable salt is formulated as described in the package insert for STIVARG®. In certain embodiments, ribociclib or a pharmaceutically acceptable salt is formulated as described in the package insert for KISQALI®. In certain embodiments, ruxolitinib or a pharmaceutically acceptable salt is formulated as described in the package insert for JAKAFI®. In certain embodiments, sorafenib or a pharmaceutically acceptable salt is formulated as described in the package insert for NEXAVAR®. In certain embodiments, sunitinib or a pharmaceutically acceptable salt is formulated as described in the package insert for SUTENT®. In certain embodiments, temsirolimus or a pharmaceutically acceptable salt is formulated as described in the package insert for TORISEL®. In certain embodiments, trametinib or a pharmaceutically acceptable salt is formulated as described in the package insert for MEKINIST®. In certain embodiments, vandetanib or a pharmaceutically acceptable salt is formulated as described in the package insert for CAPRELSA®. In certain embodiments, vemurafenib or a pharmaceutically acceptable salt is formulated as described in the package insert for ZELBORAF®.

In certain embodiments, carboplatin is formulated as described in the package insert for PARAPLATIN®. In certain embodiments, cisplatin is formulated as described in the package insert for PLATINOL®. In certain embodiments, oxaliplatin is formulated as described in the package insert for ELOXATIN®.

Methods of Use

In one embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent.

In another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a protein kinase inhibitor.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a multi-tyrosine kinase inhibitor.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3, 4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is abemaciclib, acalabrutinib, afatinib, alectinib, axitinib, binimetinib, brigatinib, bosutinib, cabozantinib, ceritinib, cobimetinib, crizotinib, dabrafenib, dacomitinib, dasatinib, encorafenib, entrectinib, erdafitinib, erlotinib, everolimus, fedratinib, gefitinib, gilteritinib, ibrutinib, imatinib, lapatinib, larotrectinib, lenvatinib, lorlatinib, midostaurin, neratinib, nilotinib, nintedanib, osimertinib, palbociclib, pazopanib, pexidartinib, ponatinib, regorafenib, ribociclib, ruxolitinib, sorafenib, sunitinib, temsirolimus, trametinib, vandetanib, or vemurafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, palbociclib, pazopanib, regorafenib, ribociclib, sorafenib, or sunitinib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, pazopanib, regorafenib, sorafenib, or sunitinib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In still another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a therapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In one embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent.

In another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a protein kinase inhibitor.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a multi-tyrosine kinase inhibitor.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is abemaciclib, acalabrutinib, afatinib, alectinib, axitinib, binimetinib, brigatinib, bosutinib, cabozantinib, ceritinib, cobimetinib, crizotinib, dabrafenib, dacomitinib, dasatinib, encorafenib, entrectinib, erdafitinib, erlotinib, everolimus, fedratinib, gefitinib, gilteritinib, ibrutinib, imatinib, lapatinib, larotrectinib, lenvatinib, lorlatinib, midostaurin, neratinib, nilotinib, nintedanib, osimertinib, palbociclib, pazopanib, pexidartinib, ponatinib, regorafenib, ribociclib, ruxolitinib, sorafenib, sunitinib, temsirolimus, trametinib, vandetanib, or vemurafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, palbociclib, pazopanib, regorafenib, ribociclib, sorafenib, or sunitinib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, pazopanib, regorafenib, sorafenib, or sunitinib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent;

wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In still another embodiment, provided herein is a method of treating, ameliorating, or preventing one or more symptoms of a disorder, disease, or condition mediated by a GPX4 in a subject, comprising administering to the subject a therapeutically effective amount of a GPX4 inhibitor and a subtherapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In one embodiment, the disorder, disease, or condition mediated by GPX4 is a proliferative disease.

In one embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent.

In another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a protein kinase inhibitor.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a multi-tyrosine kinase inhibitor.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is abemaciclib, acalabrutinib, afatinib, alectinib, axitinib, binimetinib, brigatinib, bosutinib, cabozantinib, ceritinib, cobimetinib, crizotinib, dabrafenib, dacomitinib, dasatinib, encorafenib, entrectinib, erdafitinib, erlotinib, everolimus, fedratinib, gefitinib, gilteritinib, ibrutinib, imatinib, lapatinib, larotrectinib, lenvatinib, lorlatinib, midostaurin, neratinib, nilotinib, nintedanib, osimertinib, palbociclib, pazopanib, pexidartinib, ponatinib, regorafenib, ribociclib, ruxolitinib, sorafenib, sunitinib, temsirolimus, trametinib, vandetanib, or vemurafenib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, palbociclib, pazopanib, regorafenib, ribociclib, sorafenib, or sunitinib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, pazopanib, regorafenib, sorafenib, or sunitinib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In still another embodiment, provided herein is a method of treating, ameliorating, or preventing one or more symptoms of a proliferative disease in a subject, comprising administering to the subject a therapeutically effective amount of a GPX4 inhibitor and a therapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In one embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent.

In another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a protein kinase inhibitor.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a multi-tyrosine kinase inhibitor.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is abemaciclib, acalabrutinib, afatinib, alectinib, axitinib, binimetinib, brigatinib, bosutinib, cabozantinib, ceritinib, cobimetinib, crizotinib, dabrafenib, dacomitinib, dasatinib, encorafenib, entrectinib, erdafitinib, erlotinib, everolimus, fedratinib, gefitinib, gilteritinib, ibrutinib, imatinib, lapatinib, larotrectinib, lenvatinib, lorlatinib, midostaurin, neratinib, nilotinib, nintedanib, osimertinib, palbociclib, pazopanib, pexidartinib, ponatinib, regorafenib, ribociclib, ruxolitinib, sorafenib, sunitinib, temsirolimus, trametinib, vandetanib, or vemurafenib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, palbociclib, pazopanib, regorafenib, ribociclib, sorafenib, or sunitinib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, pazopanib, regorafenib, sorafenib, or sunitinib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-

2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In still another embodiment, provided herein is a method of treating, ameliorating, or preventing one or more symptoms of a proliferative disease in a subject, comprising administering to the subject a therapeutically effective amount of a GPX4 inhibitor and a subtherapeutically effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In certain embodiments, the proliferative disease is cancer. In certain embodiments, the cancer is solid cancer. In certain embodiments, the cancer is colon cancer, liver cancer, or ovarian cancer. In certain embodiments, the cancer is colon cancer. In certain embodiments, the cancer is liver cancer. In certain embodiments, the cancer is ovarian cancer. In certain embodiments, the cancer is hematologic cancer.

In certain embodiments, the cancer is metastatic. In certain embodiments, the cancer is refractory. In certain embodiments, the cancer is relapsed. In certain embodiments, the cancer is drug resistant. In certain embodiments, the cancer is multidrug-resistant.

In certain embodiments, the subject is a mammal. In certain embodiments, the subject is a human.

In certain embodiments, the therapeutically effective amount of the GPX4 inhibitor described herein is ranging from about 0.01 to about 100 mg/kg/day, from about 0.02 to about 50 mg/kg/day, from about 0.05 to about 25 mg/kg/day, from about 0.1 to about 10 mg/kg/day, or from about 0.1 to about 5 mg/kg/day. In one embodiment, the therapeutically effective amount of the GPX4 inhibitor described herein is ranging from about 0.01 to about 100 mg/kg/day. In another embodiment, the therapeutically effective amount of the GPX4 inhibitor described herein is ranging from about 0.02 to about 50 mg/kg/day. In yet another embodiment, the therapeutically effective amount of the GPX4 inhibitor described herein is ranging from about 0.05 to about 25 mg/kg/day. In yet another embodiment, the therapeutically effective amount of the GPX4 inhibitor described herein is ranging from about 0.1 to about 10 mg/kg/day. In still another embodiment, the therapeutically effective amount of the GPX4 inhibitor described herein is ranging from about 0.1 to about 5 mg/kg/day.

It is understood that the administered dose of the GPX4 inhibitor described herein can also be expressed in units other than mg/kg/day. For example, doses for parenteral administration can be expressed as $mg/m^2/day$. One of ordinary skill in the art would readily know how to convert doses from mg/kg/day to $mg/m^2/day$ to given either the height or weight of a subject or both. For example, a dose of 1 $mg/m^2/day$ for a 65 kg human is approximately equal to 58 mg/kg/day.

In certain embodiments, the therapeutically effective amount of the GPX4 inhibitor described herein is ranging from about 1 to about 1,000 mg per day, from about 2 to about 500 mg per day, from about 5 to about 250 mg per day, from about 10 to about 200 mg per day, or from about 10 to about 100 mg per day. In one embodiment, the therapeutically effective amount of the GPX4 inhibitor described herein is ranging from about 1 to about 1,000 mg per day. In another embodiment, the therapeutically effective amount of the GPX4 inhibitor described herein is ranging from about 2 to about 500 mg per day. In yet another embodiment, the therapeutically effective amount of the GPX4 inhibitor described herein is ranging from about 5 to about 250 mg per day. In yet another embodiment, the therapeutically effective amount of the GPX4 inhibitor described herein is ranging from about 10 to about 200 mg per day. In still another embodiment, the therapeutically effective amount of the GPX4 inhibitor described herein is ranging from about 10 to about 100 mg per day.

Depending on the disease to be treated and the subject's condition, the GPX4 inhibitor described herein may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The GPX4 inhibitor described herein may be formulated in suitable dosage unit with a pharmaceutically acceptable excipient, carrier, adjuvant, or vehicle, appropriate for each route of administration.

In one embodiment, the GPX4 inhibitor described herein is administered orally. In another embodiment, the GPX4 inhibitor described herein is administered parenterally. In yet another embodiment, the GPX4 inhibitor described herein is administered intravenously. In yet another embodiment, the GPX4 inhibitor described herein is administered intramuscularly. In yet another embodiment, the GPX4 inhibitor described herein is administered subcutaneously. In still another embodiment, the GPX4 inhibitor described herein is administered topically.

In certain embodiments, the therapeutically effective amount of the anticancer agent described herein is ranging from about 0.1 to about 100 mg/kg/day, from about 0.2 to about 50 mg/kg/day, from about 0.5 to about 20 mg/kg/day, or from about 1 to about 10 mg/kg/day. In one embodiment, the therapeutically effective amount of the anticancer agent described herein is ranging from about 0.1 to about 100 mg/kg/day. In another embodiment, the therapeutically effective amount of the anticancer agent described herein is ranging from about 0.2 to about 50 mg/kg/day. In yet another embodiment, the therapeutically effective amount of the anticancer agent described herein is ranging from about 0.5 to about 20 mg/kg/day. In still another embodiment, the therapeutically effective amount of the anticancer agent described herein is ranging from about 1 to about 10 mg/kg/day.

In certain embodiments, the therapeutically effective amount of the anticancer agent described herein is ranging from about 0.1 to about 100 mg/kg/day, from about 0.2 to about 50 mg/kg/day, from about 0.5 to about 20 mg/kg/day, or from about 1 to about 10 mg/kg/day. In one embodiment, the therapeutically effective amount of the anticancer agent described herein is ranging from about 0.1 to about 100 mg/kg/day. In another embodiment, the therapeutically effective amount of the anticancer agent described herein is ranging from about 0.2 to about 50 mg/kg/day. In yet another embodiment, the therapeutically effective amount of the anticancer agent described herein is ranging from about 0.5 to about 20 mg/kg/day. In still another embodiment, the therapeutically effective amount of the anticancer agent described herein is ranging from about 1 to about 10 mg/kg/day.

It is understood that the administered dose of the anticancer agent described herein can also be expressed in units other than mg/kg/day. For example, doses for parenteral administration can be expressed as $mg/m^2/day$. One of ordinary skill in the art would readily know how to convert doses from mg/kg/day to $mg/m^2/day$ to given either the height or weight of a subject or both. For example, a dose of 1 $mg/m^2/day$ for a 65 kg human is approximately equal to 58 mg/kg/day.

In certain embodiments, the therapeutically effective amount of the anticancer agent described herein is ranging from about 1 to about 2,000 mg per day, from about 2 to about 1,000 mg per day, from about 5 to about 500 mg per day, from about 10 to about 500 mg per day, or from about 25 to about 500 mg per day. In one embodiment, the therapeutically effective amount of the anticancer agent described herein is ranging from about 1 to about 2,000 mg per day. In another embodiment, the therapeutically effective amount of the anticancer agent described herein is ranging from about 2 to about 1,000 mg per day. In yet another embodiment, the therapeutically effective amount of the anticancer agent described herein is ranging from about 5 to about 500 mg per day. In yet another embodiment, the therapeutically effective amount of the anticancer agent described herein is ranging from about 10 to about 500 mg per day. In still another embodiment, the therapeutically effective amount of the anticancer agent described herein is ranging from about 25 to about 500 mg per day.

In certain embodiments, the subtherapeutically effective amount of the anticancer agent described herein is no greater than about 0.5, no greater than about 0.2, no greater than about 0.1, or no greater than about 0.05 of the therapeutically effective amount of the anticancer agent when administered alone as monotherapy. In certain embodiments, the subtherapeutically effective amount of the anticancer agent described herein is no greater than about 0.5 of the therapeutically effective amount of the anticancer agent when administered alone as monotherapy. In certain embodiments, the subtherapeutically effective amount of the anticancer agent described herein is no greater than about 0.2 of the therapeutically effective amount of the anticancer agent when administered alone as monotherapy. In certain embodiments, the subtherapeutically effective amount of the anticancer agent described herein is no greater than about 0.1 of the therapeutically effective amount of the anticancer agent when administered alone as monotherapy. In certain embodiments, the subtherapeutically effective amount of the anticancer agent described herein is no greater than about 0.05 of the therapeutically effective amount of the anticancer agent when administered alone as monotherapy.

Depending on the disease to be treated and the subject's condition, the anticancer agent described herein may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The anticancer agent described herein may be formulated in suitable dosage unit with a pharmaceutically acceptable excipient, carrier, adjuvant, or vehicle, appropriate for each route of administration.

In one embodiment, the anticancer agent described herein is administered orally. In another embodiment, the anticancer agent described herein is administered parenterally. In yet another embodiment, the anticancer agent described herein is administered intravenously. In yet another embodiment, the anticancer agent described herein is administered intramuscularly. In yet another embodiment, the anticancer agent described herein is administered subcutaneously. In still another embodiment, the anticancer agent described herein is administered topically.

The GPX4 inhibitor and anticancer agent described herein can each independently be delivered as a single dose (e.g., a single bolus injection) or oral tablets or pills; or over time (e.g., continuous infusion over time or divided bolus doses over time). The GPX4 inhibitor and anticancer agent described herein can each independently be administered repetitively if necessary, for example, until the subject experiences stable disease or regression, or until the subject experiences disease progression or unacceptable toxicity. Stable disease or lack thereof is determined by methods known in the art such as evaluation of subject's symptoms, physical examination, visualization of the cancer that has been imaged using X-ray, CAT, PET, or MRI scan and other commonly accepted evaluation modalities.

The GPX4 inhibitor and anticancer agent described herein can each independently be administered once daily (QD) or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of the GPX4 inhibitor and anticancer agent described herein is each independently administration for one to six days per week, administration in cycles (e.g., daily administration for two to eight consecutive weeks, then a rest period with no administration for up to one week), or administration on alternate days.

In certain embodiments, the GPX4 inhibitor and anticancer agent described herein are cyclically administered to a subject. Cycling therapy involves the administration of the GPX4 inhibitor and anticancer agent for a period of time, followed by a rest for a period of time, and repeating this sequential administration. Cycling therapy can reduce the development of resistance to the treatment, avoid or reduce the side effects of the treatment, and/or improves the efficacy of the treatment.

The GPX4 inhibitor can be administered prior to (e.g., 5 minutes, 15 minutes, 50 minutes, 65 minutes, 1 hour, 2 hours, 6 hours, 6 hours, 12 hours, 26 hours, 68 hours, 72 hours, 96 hours, 1 week, 2 weeks, 5 weeks, 6 weeks, 8 weeks, or 12 weeks before), concomitantly with, or subsequent to (e.g., 5 minutes, 15 minutes, 50 minutes, 65 minutes, 1 hour, 2 hours, 6 hours, 12 hours, 26 hours, 68 hours, 72 hours, 96 hours, 1 week, 2 weeks, 5 weeks, 6 weeks, 8 weeks, or 12 weeks after) the administration of the anticancer agent to the subject. In one embodiment, the GPX4 inhibitor is administered concurrently with the anticancer agent. In another embodiment, the GPX4 inhibitor is administered separately with the anticancer agent. In yet another embodiment, the GPX4 inhibitor is administered sequentially with the anticancer agent. In yet another embodiment, the GPX4 inhibitor is administered before the anticancer agent. In yet another embodiment, the GPX4 inhibitor is administered after the anticancer agent.

The route of administration of the GPX4 inhibitor is independent of the route of administration of the anticancer agent. In one embodiment, the GPX4 inhibitor described herein is administered orally. In another embodiment, the GPX4 inhibitor described herein is administered intravenously. Thus, in accordance with these embodiments, the GPX4 inhibitor described herein is administered orally or intravenously, and the anticancer agent can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, the GPX4 inhibitor and anticancer agent described herein are administered by the same mode of administration, orally or by IV. In another embodiment, the GPX4 inhibitor described herein is administered by one mode of administration, e.g., by IV, whereas the anticancer agent is administered by another mode of administration, e.g., orally.

In one embodiment, provided herein is a method of inhibiting the growth of a cell, comprising contacting the cell with an effective amount of a GPX4 inhibitor and an effective amount of an anticancer agent.

In another embodiment, provided herein is a method of inhibiting the growth of a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a protein kinase inhibitor.

In yet another embodiment, provided herein is a method of inhibiting the growth of a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a multi-tyrosine kinase inhibitor.

In yet another embodiment, provided herein is a method of inhibiting the growth of a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is abemaciclib, acalabrutinib, afatinib, alectinib, axitinib, binimetinib, brigatinib, bosutinib, cabozantinib, ceritinib, cobimetinib, crizotinib, dabrafenib, dacomitinib, dasatinib, encorafenib, entrectinib, erdafitinib, erlotinib, everolimus, fedratinib, gefitinib, gilteritinib, ibrutinib, imatinib, lapatinib, larotrectinib, lenvatinib, lorlatinib, midostaurin, neratinib, nilotinib, nintedanib, osimertinib, palbociclib, pazopanib, pexidartinib, ponatinib, regorafenib, ribociclib, ruxolitinib, sorafenib, sunitinib, temsirolimus, trametinib, vandetanib, or vemurafenib.

In yet another embodiment, provided herein is a method of inhibiting the growth of a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, palbociclib, pazopanib, regorafenib, ribociclib, sorafenib, or sunitinib.

In yet another embodiment, provided herein is a method of inhibiting the growth of a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, pazopanib, regorafenib, sorafenib, or sunitinib.

In yet another embodiment, provided herein is a method of inhibiting the growth of a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inhibiting the growth of a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indol-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inhibiting the growth of a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indol-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of inhibiting the growth of a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indol-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of inhibiting the growth of a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indol-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of inhibiting the growth of a cell, comprising contacting the cell with an effective amount of a GPX4 inhibitor and an effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inhibiting the growth of a cell, comprising contacting the cell with an effective amount of a GPX4 inhibitor and an effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of inhibiting the growth of a cell, comprising contacting the cell with an effective amount of a GPX4 inhibitor and an effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of inhibiting the growth of a cell, comprising contacting the cell with an effective amount of a GPX4 inhibitor and an effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of inhibiting the growth of a cell, comprising contacting the cell with an effective amount of a GPX4 inhibitor and an effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inhibiting the growth of a cell, comprising contacting the cell with an effective amount of a GPX4 inhibitor and an effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of inhibiting the growth of a cell, comprising contacting the cell with an effective amount of a GPX4 inhibitor and an effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In still another embodiment, provided herein is a method of inhibiting the growth of a cell, comprising contacting the cell with an effective amount of a GPX4 inhibitor and an effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In one embodiment, provided herein is a method of inhibiting the growth of a cell, comprising contacting the cell with an effective amount of a GPX4 inhibitor and a subeffective amount of an anticancer agent.

In another embodiment, provided herein is a method of inhibiting the growth of a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a protein kinase inhibitor.

In yet another embodiment, provided herein is a method of inhibiting the growth of a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a multi-tyrosine kinase inhibitor.

In yet another embodiment, provided herein is a method of inhibiting the growth of a cell, comprising contacting the cell with an effective amount of a GPX4 inhibitor and an subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is abemaciclib, acalabrutinib, afatinib, alectinib, axitinib, binimetinib, brigatinib, bosutinib, cabozantinib, ceritinib, cobimetinib, crizotinib, dabrafenib, dacomitinib, dasatinib, encorafenib, entrectinib, erdafitinib, erlotinib, everolimus, fedratinib, gefitinib, gilteritinib, ibrutinib, imatinib, lapatinib, larotrectinib, lenvatinib, lorlatinib, midostaurin, neratinib, nilotinib, nintedanib, osimertinib, palbociclib, pazopanib, pexidartinib, ponatinib, regorafenib, ribociclib, ruxolitinib, sorafenib, sunitinib, temsirolimus, trametinib, vandetanib, or vemurafenib.

In yet another embodiment, provided herein is a method of inhibiting the growth of a cell, comprising contacting the cell with an effective amount of a GPX4 inhibitor and an subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, palbociclib, pazopanib, regorafenib, ribociclib, sorafenib, or sunitinib.

In yet another embodiment, provided herein is a method of inhibiting the growth of a cell, comprising contacting the cell with an effective amount of a GPX4 inhibitor and an subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, pazopanib, regorafenib, sorafenib, or sunitinib.

In yet another embodiment, provided herein is a method of inhibiting the growth of a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inhibiting the growth of a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inhibiting the growth of a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of inhibiting the growth of a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of inhibiting the growth of a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of inhibiting the growth of a cell, comprising contacting the cell with an effective amount of a GPX4 inhibitor and a subeffective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inhibiting the growth of a cell, comprising contacting the cell with an effective amount of a GPX4 inhibitor and a subeffective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of inhibiting the growth of a cell, comprising contacting the cell with an effective amount of a GPX4 inhibitor and a subeffective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of inhibiting the growth of a cell, comprising contacting the cell with an effective amount of a GPX4 inhibitor and a subeffective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of inhibiting the growth of a cell, comprising contacting the cell with an effective amount of a GPX4 inhibitor and a subeffective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inhibiting the growth of a cell, comprising contacting the cell with an effective amount of a GPX4 inhibitor and a subeffective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of inhibiting the growth of a cell, comprising contacting the cell with an effective amount of a GPX4 inhibitor and a subeffective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In still another embodiment, provided herein is a method of inhibiting the growth of a cell, comprising contacting the cell with an effective amount of a GPX4 inhibitor and a subeffective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In one embodiment, provided herein is a method of inducing ferroptosis in a cell, comprising contacting the cell with an effective amount of a GPX4 inhibitor and an effective amount of an anticancer agent.

In another embodiment, provided herein is a method of inducing ferroptosis in a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a protein kinase inhibitor.

In yet another embodiment, provided herein is a method of inducing ferroptosis in a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a multi-tyrosine kinase inhibitor.

In yet another embodiment, provided herein is a method of inducing ferroptosis in a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is abemaciclib, acalabrutinib, afatinib, alectinib, axitinib, binimetinib, brigatinib, bosutinib, cabozantinib, ceritinib, cobimetinib, crizotinib, dabrafenib, dacomitinib, dasatinib, encorafenib, entrectinib, erdafitinib, erlotinib, everolimus, fedratinib, gefitinib, gilteritinib, ibrutinib, imatinib, lapatinib, larotrectinib, lenvatinib, lorlatinib, midostaurin, neratinib, nilotinib, nintedanib, osimertinib, palbociclib, pazopanib, pexidartinib, ponatinib, regorafenib, ribociclib, ruxolitinib, sorafenib, sunitinib, temsirolimus, trametinib, vandetanib, or vemurafenib.

In yet another embodiment, provided herein is a method of inducing ferroptosis in a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, palbociclib, pazopanib, regorafenib, ribociclib, sorafenib, or sunitinib.

In yet another embodiment, provided herein is a method of inducing ferroptosis in a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, pazopanib, regorafenib, sorafenib, or sunitinib.

In yet another embodiment, provided herein is a method of inducing ferroptosis in a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inducing ferroptosis in a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inducing ferroptosis in a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of inducing ferroptosis in a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of inducing ferroptosis in a cell, comprising contacting the cell with an effective amount of a GPX4 inhibitor and an effective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of inducing ferroptosis in a cell, comprising contacting the cell with an effective amount of a GPX4 inhibitor and an effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inducing ferroptosis in a cell, comprising contacting the cell with an effective amount of a GPX4 inhibitor and an effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of inducing ferroptosis in a cell, comprising contacting the cell with an effective amount of a GPX4 inhibitor and an effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of inducing ferroptosis in a cell, comprising contacting the cell with an effective amount of a GPX4 inhibitor and an effective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of inducing ferroptosis in a cell, comprising contacting the cell with an effective amount of a GPX4 inhibitor and an effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inducing ferroptosis in a cell, comprising contacting the cell with an effective amount of a GPX4 inhibitor and an effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of inducing ferroptosis in a cell, comprising contacting the cell with an effective amount of a GPX4 inhibitor and an effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In still another embodiment, provided herein is a method of inducing ferroptosis in a cell, comprising contacting the cell with an effective amount of a GPX4 inhibitor and an effective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In one embodiment, provided herein is a method of inducing ferroptosis in a cell, comprising contacting the cell with an effective amount of a GPX4 inhibitor and a subeffective amount of an anticancer agent.

In another embodiment, provided herein is a method of inducing ferroptosis in a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a protein kinase inhibitor.

In yet another embodiment, provided herein is a method of inducing ferroptosis in a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl) benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is a multi-tyrosine kinase inhibitor.

In yet another embodiment, provided herein is a method of inducing ferroptosis in a cell, comprising contacting the cell with an effective amount of a GPX4 inhibitor and an subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is abemaciclib, acalabrutinib, afatinib, alectinib, axitinib, binimetinib, brigatinib, bosutinib, cabozantinib, ceritinib, cobimetinib, crizotinib, dabrafenib, dacomitinib, dasatinib, encorafenib, entrectinib, erdafitinib, erlotinib, everolimus, fedratinib, gefitinib, gilteritinib, ibrutinib, imatinib, lapatinib, larotrectinib, lenvatinib, lorlatinib, midostaurin, neratinib, nilotinib, nintedanib, osimertinib, palbociclib, pazopanib, pexidartinib, ponatinib, regorafenib, ribociclib, ruxolitinib, sorafenib, sunitinib, temsirolimus, trametinib, vandetanib, or vemurafenib.

In yet another embodiment, provided herein is a method of inducing ferroptosis in a cell, comprising contacting the cell with an effective amount of a GPX4 inhibitor and an subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, palbociclib, pazopanib, regorafenib, ribociclib, sorafenib, or sunitinib.

In yet another embodiment, provided herein is a method of inducing ferroptosis in a cell, comprising contacting the cell with an effective amount of a GPX4 inhibitor and an subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is axitinib, gefitinib, imatinib, lenvatinib, neratinib, nintedanib, pazopanib, regorafenib, sorafenib, or sunitinib.

In yet another embodiment, provided herein is a method of inducing ferroptosis in a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, methyl 4-((3R)-3-(hydroxymethyl)-2-propioloyl-2,3,4,9-tetrahydro-1H-pyrido[3,4-b]indol-1-yl)benzoate A2, or N-(1-(4-aminophenyl)-2-(tert-butylamino)-2-oxoethyl)-N-(3-chloro-4-methoxyphenyl)propiolamide A3; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inducing ferroptosis in a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inducing ferroptosis in a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of inducing ferroptosis in a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of inducing ferroptosis in a cell, comprising contacting the cell with an effective amount of a GPX4 inhibitor and a subeffective amount of an anticancer agent; wherein the GPX4 is methyl (3R)-2-(2-chloroacetyl)-2,3,4,9-tetrahydro-1-[4-(methoxycarbonyl)phenyl]-1H-pyrido[3,4-b]indole-3-carboxylate A1, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of inducing ferroptosis in a cell, comprising contacting the cell with an effective amount of a GPX4 inhibitor and a subeffective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inducing ferroptosis in a cell, comprising contacting the cell with an effective amount of a GPX4 inhibitor and a subeffective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of inducing ferroptosis in a cell, comprising contacting the cell with an effective amount of a GPX4 inhibitor and a subeffective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In yet another embodiment, provided herein is a method of inducing ferroptosis in a cell, comprising contacting the cell with an effective amount of a GPX4 inhibitor and a subeffective amount of an anticancer agent; wherein the GPX4 is methyl 4-((3R)-3-(hydroxymethyl)-2-propioloyl-2,3,4,9-tetrahydro-1H-pyrido[3,4-b]indol-1-yl)benzoate A2, or a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In yet another embodiment, provided herein is a method of inducing ferroptosis in a cell, comprising contacting the cell with an effective amount of a GPX4 inhibitor and a subeffective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib, regorafenib, or sorafenib.

In yet another embodiment, provided herein is a method of inducing ferroptosis in a cell, comprising contacting the cell with an effective amount of a GPX4 inhibitor and a subeffective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is neratinib.

In yet another embodiment, provided herein is a method of inducing ferroptosis in a cell, comprising contacting the cell with an effective amount of a GPX4 inhibitor and a subeffective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is regorafenib.

In still another embodiment, provided herein is a method of inducing ferroptosis in a cell, comprising contacting the cell with an effective amount of a GPX4 inhibitor and a subeffective amount of an anticancer agent; wherein the GPX4 is N-(1-(4-aminophenyl)-2-(tert-butylamino)-2-oxoethyl)-N-(3-chloro-4-methoxyphenyl)-propiolamide A3, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and wherein the anticancer agent is sorafenib.

In one embodiment, the cell is a cancerous cell. In another embodiment, the cell is a cell of solid cancer. In yet another embodiment, the cell is a cell of colon cancer, liver cancer, or ovarian cancer. In yet another embodiment, the cell is a cell of colon cancer. In yet another embodiment, the cell is a cell of liver cancer. In yet another embodiment, the cell is a cell of ovarian cancer. In still another embodiment, the cell is a cell of hematologic cancer.

In certain embodiments, the cell is a mammalian cell. In certain embodiments, the cell is a human cell.

In certain embodiments, the effective amount of the GPX4 inhibitor described herein is ranging from about 0.01 to about 100 mg/kg/day, from about 0.02 to about 50 mg/kg/day, from about 0.05 to about 25 mg/kg/day, from about 0.1 to about 10 mg/kg/day, or from about 0.1 to about 5 mg/kg/day. In one embodiment, the effective amount of the GPX4 inhibitor described herein is ranging from about 0.01 to about 100 mg/kg/day. In another embodiment, the effective amount of the GPX4 inhibitor described herein is ranging from about 0.02 to about 50 mg/kg/day. In yet another embodiment, the effective amount of the GPX4 inhibitor described herein is ranging from about 0.05 to about 25 mg/kg/day. In yet another embodiment, the effective amount of the GPX4 inhibitor described herein is ranging from about 0.1 to about 10 mg/kg/day. In still another embodiment, the effective amount of the GPX4 inhibitor described herein is ranging from about 0.1 to about 5 mg/kg/day.

In certain embodiments, the effective amount of the GPX4 inhibitor described herein is ranging from about 1 to about 1,000 mg per day, from about 2 to about 500 mg per day, from about 5 to about 250 mg per day, from about 10 to about 200 mg per day, or from about 10 to about 100 mg per day. In one embodiment, the effective amount of the GPX4 inhibitor described herein is ranging from about 1 to about 1,000 mg per day. In another embodiment, the effective amount of the GPX4 inhibitor described herein is ranging from about 2 to about 500 mg per day. In yet another embodiment, the effective amount of the GPX4 inhibitor described herein is ranging from about 5 to about 250 mg per day. In yet another embodiment, the effective amount of the GPX4 inhibitor described herein is ranging from about 10 to about 200 mg per day. In still another embodiment, the effective amount of the GPX4 inhibitor described herein is ranging from about 10 to about 100 mg per day.

In certain embodiments, the effective amount of the GPX4 inhibitor described herein is ranging from about 10 pM to about 100 μM, from about 50 pM to about 20 μM, from about 0.1 nM to about 10 μM, from about 0.2 nM to about 5 μM, from about 0.5 nM to about 2 μM, or from about 1 to about 1,000 nM. In certain embodiments, the effective amount of the GPX4 inhibitor described herein is ranging from about 10 pM to about 100 μM. In certain embodiments, the effective amount of the GPX4 inhibitor described herein is ranging from about 50 pM to about 20 μM. In certain embodiments, the effective amount of the GPX4 inhibitor described herein is ranging from about 0.1 nM to about 10 μM. In certain embodiments, the effective amount of the GPX4 inhibitor described herein is ranging from about 0.2 nM to about 5 μM. In certain embodiments, the effective amount of the GPX4 inhibitor described herein is ranging from about 0.5 nM to about 2 μM. In certain embodiments, the effective amount of the GPX4 inhibitor described herein is ranging from about 1 to about 1,000 nM.

In certain embodiments, the subeffective amount of the anticancer agent described herein is no greater than about 0.5, no greater than about 0.2, no greater than about 0.1, or no greater than about 0.05 of the therapeutically effective amount of the anticancer agent when administered alone as monotherapy. In certain embodiments, the subeffective amount of the anticancer agent described herein is no greater than about 0.5 of the therapeutically effective amount of the anticancer agent when administered alone as monotherapy. In certain embodiments, the subeffective amount of the anticancer agent described herein is no greater than about 0.2 of the therapeutically effective amount of the anticancer agent when administered alone as monotherapy. In certain embodiments, the subeffective amount of the anticancer agent described herein is no greater than about 0.1 of the therapeutically effective amount of the anticancer agent when administered alone as monotherapy. In certain embodiments, the subeffective amount of the anticancer agent described herein is no greater than about 0.05 of the therapeutically effective amount of the anticancer agent when administered alone as monotherapy.

The disclosure will be further understood by the following non-limiting examples.

EXAMPLES

As used herein, the symbols and conventions used in example(s), regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); nM (nanomolar); pM (picomolar); mmol (millimoles); h (hour or hours); and min (minutes).

Example 1

Cell Proliferation Assay

Figure 2:
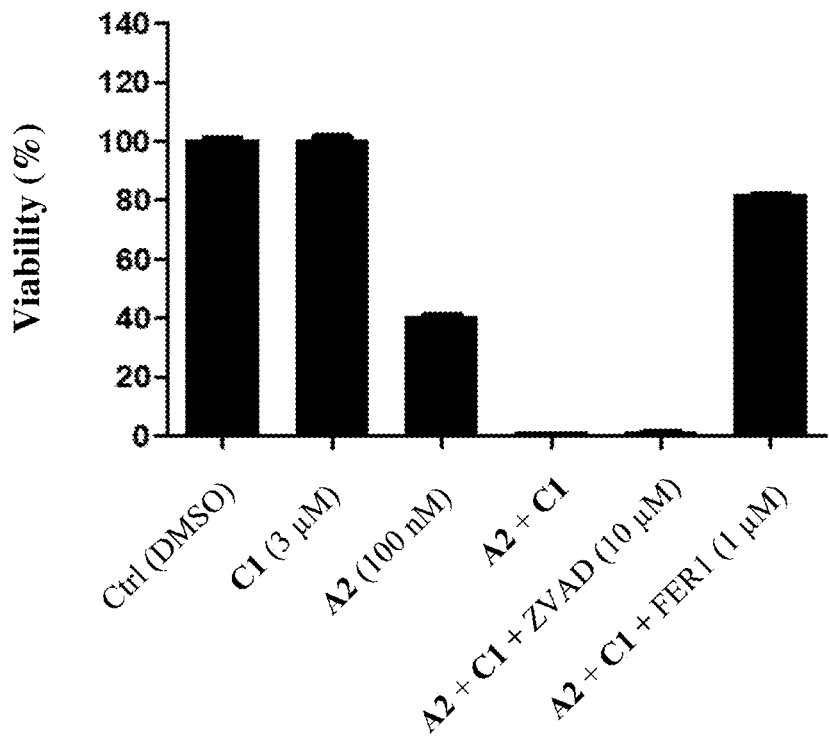
FIG. 2 shows the effects of GPX4 inhibitor A2 (100 nM) alone and in combination with sorafenib C1 (3 µM) on the viability of Huh-7 cells.
Figure 3:
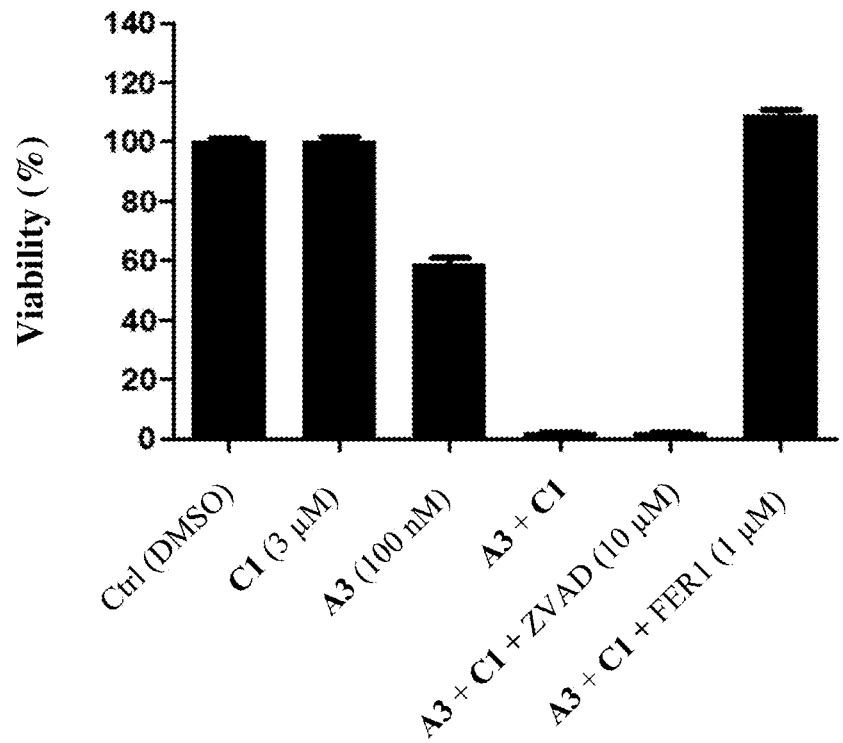
FIG. 3 shows the effects of GPX4 inhibitor A3 (100 nM) alone and in combination with sorafenib C1 (3 µM) on the viability of Huh-7 cells.
Figure 4:
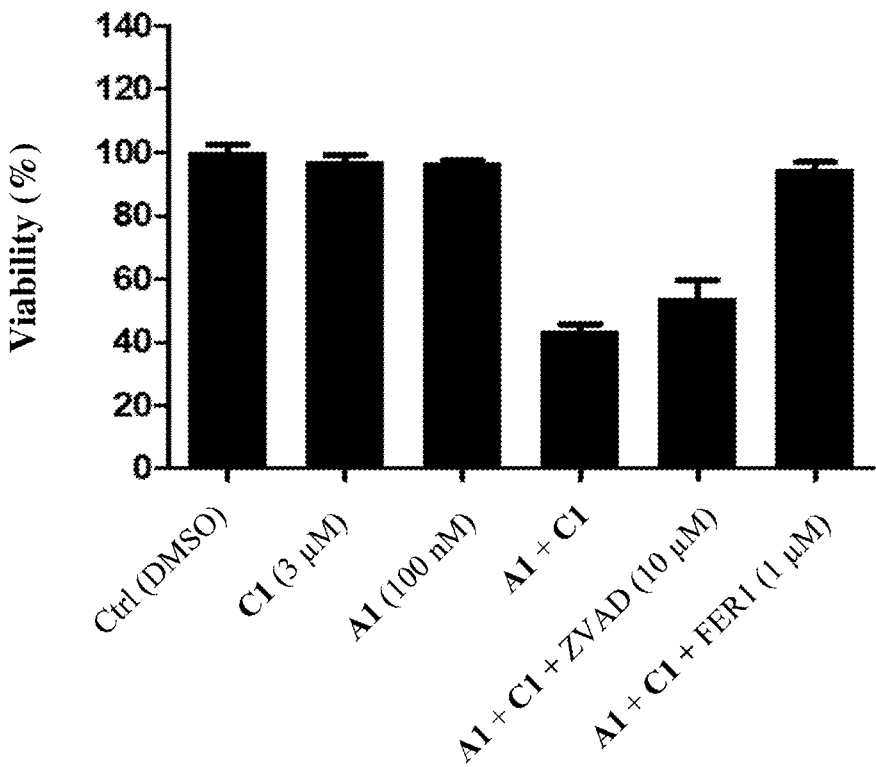
FIG. 4 shows the effects of GPX4 inhibitor A1 (100 nM) alone and in combination with sorafenib C1 (3 µM) on the viability of HT-29 cells.
Figure 5:
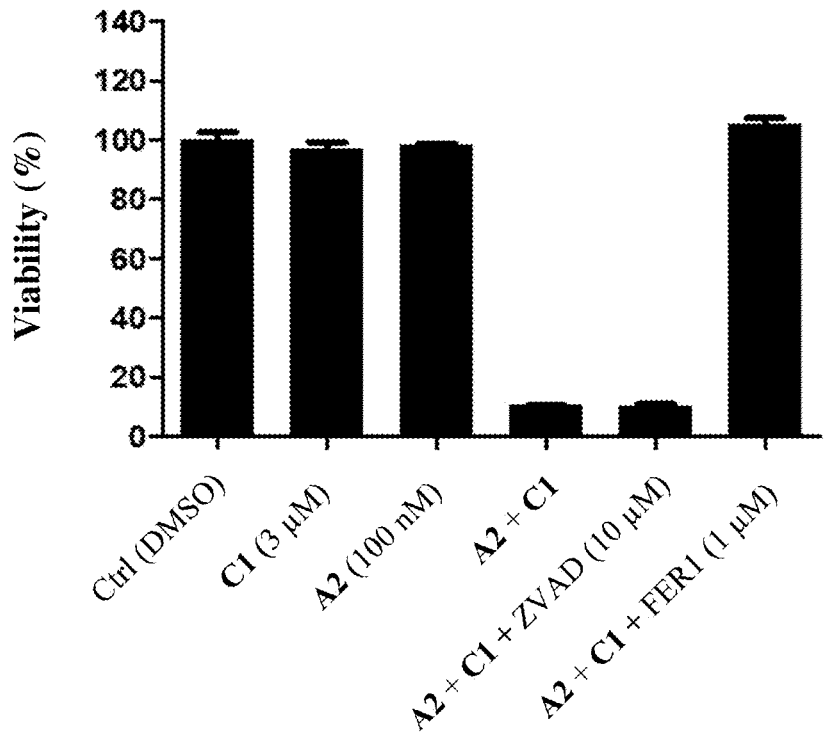
FIG. 5 shows the effects of GPX4 inhibitor A2 (100 nM) alone and in combination with sorafenib C1 (3 µM) on the viability of HT-29 cells.
Figure 6:
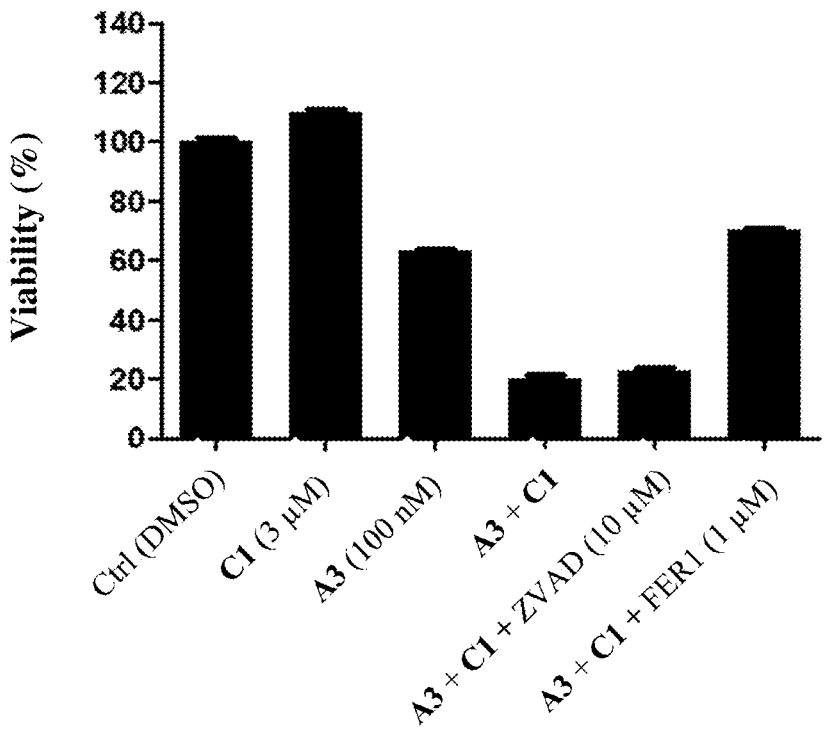
FIG. 6 shows the effects of GPX4 inhibitor A3 (100 nM) alone and in combination with sorafenib C1 (3 µM) on the viability of HT-29 cells.

The activity of a combination of a GPX4 inhibitor (e.g., compound A1, A2, or A3) and a tyrosine kinase inhibitor (e.g., neratinib, regorafenib, or sorafenib) was determined in a cell proliferation assay using cancerous cell lines (e.g., HT-29 (colorectal adenocarcinoma), Hub-7 (hepatocellular carcinoma), or OVCAR-8 (ovarian adenocarcinoma)). Cells of each cell line were seeded in a 96-well tissue culture plate. After incubated overnight, a compound or a combination was added at predetermined concentration(s). After the cells were incubated for 24 h, cell viability was determined using a CELL-TITER GLO® assay. The CELL-TITER GLO® reagent (50 μL) was added to each well and the luminescence was measured by a multimode microplate reader after a brief period of shaking. $EC_{50}$ values were determined from dose response curves. The results are shown in FIGS. 1 to 6 and Table 1. The results in FIGS. 1 to 6 shown that shows the effects of GPX4 inhibitor A1 (100 nM) alone or in combination with sorafenib C1 (3 μM) on the viability of Huh-7 cells, where Fer-1 represents ferrostatin-1, a ferroptosis inhibitor (see Skouta et al., *J. Am. Chem. Soc.* 2014, 136, 4551-4556); and ZVAD represents Z-VAD-FMK, an apoptosis inhibitor (see Yang et al., *Br. J. Pharmacol.* 2003, 140, 402-412). As shown in FIGS. 1 to 6, Fer-1 (a ferroptosis inhibitor) was able to rescue HT-29 and Huh-7 cells from cell death induced by GPX4 inhibitor A1, A2, or A3 in combination with sorafenib C1, whereas ZVAD (an apoptosis inhibitor) could not.

TABLE 1

| Inhibition of Cell Proliferation | | | |
|---|---|---|---|
| | | Combination | |
| GPX4 Inhibitor | Monotherapy | +C2 (10 μM) | +C3 (3 μM) |
| A1 | 8.0 μM | 57 nM | 0.97 μM |
| A2 | 22.5 μM | 97 nM | 1.3 μM |
| A3 | 5.7 μM | 207 nM | 1.8 μM |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of abrogating or alleviating cancer in a subject, comprising administering to the subject in need thereof a therapeutically effective amount of a glutathione peroxidase 4 inhibitor and a therapeutically effective amount or a subtherapeutically effective amount of an anticancer agent; wherein the cancer is colorectal adenocarcinoma, hepatocellular carcinoma, or ovarian adenocarcinoma; wherein the glutathione peroxidase 4 inhibitor is methyl 4-((3R)-3-(hydroxymethyl)-2-propioloyl-2,3,4,9-tetrahydro-1H-pyrido[3,4-b]indol-1-yl)benzoate or N-(1-(4-aminophenyl)-2-(tert-butylamino)-2-oxoethyl)-N-(3-chloro-4-methoxyphenyl)-propiolamide; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof; and wherein the anticancer agent is neratinib, regorafenib, or sorafenib.

2. The method of claim 1, wherein the therapeutically effective amount of the anticancer agent is ranging from about 0.1 to about 100 mg/kg/day or from about 1 to about 2,000 mg per day.

3. The method of claim 1, wherein the cancer is metastatic, refractory, and/or relapsed.

4. The method of claim 1, wherein the cancer is drug resistant or multidrug-resistant.

5. The method of claim 1, wherein the therapeutically effective amount of the glutathione peroxidase 4 inhibitor is ranging from about 0.01 to about 100 mg/kg/day or from about 1 to about 1,000 mg per day.

6. The method of claim 1, wherein the glutathione peroxidase 4 inhibitor is administered orally.

7. The method of claim 1, wherein the anticancer agent is neratinib.

8. The method of claim 1, wherein the anticancer agent is administered orally.

9. The method of claim 1, wherein the subject is a human.

10. A method of inhibiting the growth of a cancerous cell or inducing ferroptosis in a cancerous cell, comprising contacting the cell with an effective amount of a GPX4 inhibitor and an effective amount or a subeffective amount of an anticancer agent; wherein the glutathione peroxidase 4 inhibitor is methyl 4-((3R)-3-(hydroxymethyl)-2-propioloyl-2,3,4,9-tetrahydro-1H-pyrido[3,4-b]indol-1-yl)benzoate or N-(1-(4-aminophenyl)-2-(tert-butylamino)-2-oxoethyl)-N-(3-chloro-4-methoxyphenyl)-propiolamide; or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof; and wherein the anticancer agent is neratinib, regorafenib, or sorafenib.

11. The method of claim 1, wherein the glutathione peroxidase 4 inhibitor is methyl 4-((3R)-3-(hydroxymethyl)-2-propioloyl-2,3,4,9-tetrahydro-1H-pyrido[3,4-b]indol-1-yl)benzoate; or an enantiomer, a mixture of enantiomers, a diastereomer, a mixture of two or more diastereomers, a tautomer, a mixture of two or more tautomers, or an isotopic variant thereof.

12. The method of claim 1, wherein the glutathione peroxidase 4 inhibitor is N-(1-(4-aminophenyl)-2-(tert-butylamino)-2-oxoethyl)-N-(3-chloro-4-methoxyphenyl)-propiolamide; or an enantiomer, a mixture of enantiomers, a diastereomer, a mixture of two or more diastereomers, a tautomer, a mixture of two or more tautomers, or an isotopic variant thereof.

13. The method of claim 1, wherein the anticancer agent is regorafenib.

14. The method of claim 1, wherein the anticancer agent is sorafenib.

15. The method of claim 10, wherein the glutathione peroxidase 4 inhibitor is methyl 4-((3R)-3-(hydroxymethyl)-2-propioloyl-2,3,4,9-tetrahydro-1H-pyrido[3,4-b]indol-1-yl)benzoate; or an enantiomer, a mixture of enantiomers, a diastereomer, a mixture of two or more diastereomers, a tautomer, a mixture of two or more tautomers, or an isotopic variant thereof.

16. The method of claim 10, wherein the glutathione peroxidase 4 inhibitor is N-(1-(4-aminophenyl)-2-(tert-butylamino)-2-oxoethyl)-N-(3-chloro-4-methoxyphenyl)-propiolamide; or an enantiomer, a mixture of enantiomers, a diastereomer, a mixture of two or more diastereomers, a tautomer, a mixture of two or more tautomers, or an isotopic variant thereof.

17. The method of claim 1, wherein the subtherapeutically effective amount of the anticancer agent is no greater than about 0.5 of the therapeutically effective amount of the anticancer agent when administered alone as monotherapy.

* * * * *